(12) United States Patent
Chang

(10) Patent No.: US 11,944,455 B2
(45) Date of Patent: *Apr. 2, 2024

(54) SYSTEMS AND METHODS FOR PERFORMING AN ELECTROCARDIOGRAM

(71) Applicant: LOS ANGELES BIOMEDICAL RESEARCH INSTITUTE AT HARBOR-UCLA MEDICAL CENTER, Torrance, CA (US)

(72) Inventor: Ruey-Kang Chang, Diamond Bar, CA (US)

(73) Assignee: LOS ANGELES BIOMEDICAL RESEARCH INSTITUTE AT HARBOR-UCLA MEDICAL CENTER, Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/963,131

(22) Filed: Oct. 10, 2022

(65) Prior Publication Data

US 2023/0034656 A1 Feb. 2, 2023

Related U.S. Application Data

(63) Continuation of application No. 15/098,180, filed on Apr. 13, 2016, now Pat. No. 11,471,107.

(Continued)

(51) Int. Cl.
*A61B 5/05* (2021.01)
*A61B 5/00* (2006.01)
(Continued)

(52) U.S. Cl.
CPC .......... *A61B 5/6841* (2013.01); *A61B 5/0006* (2013.01); *A61B 5/259* (2021.01);
(Continued)

(58) Field of Classification Search
CPC . A61B 5/6841; A61B 5/0006; A61B 5/04012; A61B 5/04085; A61B 5/04087;
(Continued)

(56) References Cited

U.S. PATENT DOCUMENTS

| 6,415,169 B1 | 7/2002 | Kornrumpf et al. |
| 6,453,186 B1 * | 9/2002 | Lovejoy ................. A61B 5/282 |
| | | 600/386 |

(Continued)

FOREIGN PATENT DOCUMENTS

| EP | 0855167 B1 | 1/2005 |
| JP | 2002-325740 A2 | 11/2002 |

(Continued)

OTHER PUBLICATIONS

Intellectual Property Administration of P. R.C., Official Action issued in CN Patent Application No. 201680022545.X, dated Nov. 17, 2022, pp. 1-6.

(Continued)

*Primary Examiner* — Adam Z Minchella
(74) *Attorney, Agent, or Firm* — Pillsbury Winthrop Shaw Pittman LLP

(57) ABSTRACT

A system and method for performing an electrocardiogram is described herein. The system may include one or more of an electrode strip, a data recorder, a connector, one or more computing platforms, and/or other components. The electrode strip may include multiple electrodes configured to provide signals conveying information associated with electrocardiograms. The multiple electrodes may be integrated into the electrode strip. The data recorder may be configured to receive and record information associated with electrocardiograms. Information associated with electrocardiograms may be communicated from the electrode strip to the data recorder via a connector. The connector may include a (Continued)

cableless connector. In some implementations, the information associated with electrocardiograms may be transmitted to one or more computing platforms.

23 Claims, 8 Drawing Sheets

Related U.S. Application Data

(60) Provisional application No. 62/148,334, filed on Apr. 16, 2015.

(51) Int. Cl.
*A61B 5/259* (2021.01)
*A61B 5/282* (2021.01)
*A61B 5/30* (2021.01)
*A61B 5/316* (2021.01)
*A61B 5/333* (2021.01)
*A61B 5/339* (2021.01)

(52) U.S. Cl.
CPC .............. *A61B 5/282* (2021.01); *A61B 5/303* (2021.01); *A61B 5/316* (2021.01); *A61B 5/333* (2021.01); *A61B 5/339* (2021.01); *A61B 5/6823* (2013.01); *A61B 2503/04* (2013.01); *A61B 2503/06* (2013.01); *A61B 2503/40* (2013.01); *A61B 2560/0443* (2013.01); *A61B 2562/164* (2013.01); *A61B 2562/166* (2013.01); *A61B 2562/222* (2013.01); *A61B 2562/227* (2013.01)

(58) Field of Classification Search
CPC ... A61B 5/04286; A61B 5/0432; A61B 5/044; A61B 5/6823; A61B 2503/04; A61B 2503/06; A61B 2503/40; A61B 2560/0443; A61B 2562/164; A61B 2562/166; A61B 2562/222; A61B 2562/227
See application file for complete search history.

(56) References Cited

U.S. PATENT DOCUMENTS

| | | |
|---|---|---|
| 6,745,061 B1 | 6/2004 | Hicks et al. |
| 6,847,836 B1 | 1/2005 | Sujdak |
| 7,206,630 B1 | 4/2007 | Tarler |
| 7,266,405 B1 | 9/2007 | Alroy et al. |
| 7,979,110 B1 | 7/2011 | Krzypow et al. |
| 8,660,630 B2 | 2/2014 | Chang |
| 8,868,152 B2 | 10/2014 | Burns et al. |
| 2004/0176674 A1* | 9/2004 | Nazeri ............... A61B 5/061 600/382 |
| 2005/0177052 A1 | 8/2005 | Istvan et al. |
| 2006/0229523 A1* | 10/2006 | Barr ................. A61B 5/332 600/509 |
| 2009/0264792 A1 | 10/2009 | Mazar |
| 2010/0174204 A1* | 7/2010 | Danteny .............. A61B 5/411 600/509 |
| 2011/0172503 A1 | 7/2011 | Knepper et al. |
| 2011/0237922 A1 | 9/2011 | Parker, III et al. |
| 2011/0270069 A1 | 11/2011 | Acquista |
| 2011/0270100 A1* | 11/2011 | Chang ............... A61B 5/0006 600/509 |
| 2012/0089000 A1* | 4/2012 | Bishay ............... A61B 5/301 600/391 |
| 2012/0215077 A1 | 8/2012 | Geissler et al. |
| 2013/0099918 A1 | 4/2013 | Dunst |
| 2013/0317333 A1 | 11/2013 | Yang et al. |
| 2014/0066741 A1 | 3/2014 | Peterson et al. |
| 2014/0073979 A1* | 3/2014 | Inciardi ............... G16Z 99/00 600/509 |
| 2014/0257050 A1 | 3/2014 | Kuroda et al. |
| 2015/0022372 A1 | 1/2015 | Vosch |
| 2016/0262649 A1* | 9/2016 | Hayes-Gill .......... A61B 5/6833 |

FOREIGN PATENT DOCUMENTS

| | | |
|---|---|---|
| JP | 2003-310563 A2 | 11/2003 |
| JP | 2005-137456 A2 | 6/2005 |
| JP | 2006-500964 A | 1/2006 |
| JP | 6780828 B2 | 10/2020 |
| WO | 2016/168269 A1 | 10/2016 |

OTHER PUBLICATIONS

Japanese Intellectual Patent Office, Official Action issued in JP 2020-111507, dated Aug. 3, 2021, pp. 1-2, (English translation).
Japanese Intellectual Property Office, Office Action issued in JP 2017-553357, dated Oct. 29, 2019, pp. 1-6 (English translation).
The State Intellectual Property Office of P. R. C., Office Action issued in CN 201680022545.X, dated Oct. 9, 2019, pp. 1-11.
European Patent Office, Supplementary Partial European Search Report for EP 16780604.1, dated Nov. 12, 2018, pp. 1-13.
International Preliminary Report on Patentability PCT/US2016/027246 dated Oct. 17, 2017.
International Search Report PCT/US2016/027246 dated Jul. 5, 2016.
Written Opinion of the International Searching Authority PCT/US2016/027246 dated Jul. 5, 2016.

* cited by examiner

SYSTEMS AND METHODS FOR PERFORMING AN ELECTROCARDIOGRAM

CROSS-REFERENCE TO RELATED PATENT APPLICATIONS

This application is a continuation application of application Ser. No. 15/098,180, filed Apr. 13, 2016 and entitled "SYSTEMS AND METHODS FOR PERFORMING AN ELECTROCARDIOGRAM", which claims the priority benefit of U.S. Provisional Patent Application No. 62/148,344 filed Apr. 16, 2015 and entitled "SYSTEMS AND METHODS FOR PERFORMING AN ELECTROCARDIOGRAM," the entire contents of the foregoing applications are incorporated herein by reference, including all text and drawings.

FIELD OF THE DISCLOSURE

This disclosure relates to systems and methods for performing an electrocardiogram.

BACKGROUND

Typically, electrocardiograms (ECGs) are performed in a clinical setting by trained clinicians, such as registered nurses, doctors, nurses' assistants, or ECG technicians. To perform an ECG, the clinician may place electrodes in specific anatomical locations on the subject. For a standard 12-lead electrocardiogram, there may be ten or more electrodes that must be placed. Once the electrodes are placed, the clinician may connect each electrode with its corresponding cable. As such, electrocardiograms are often subject to human error due to misplaced electrodes and/or mismatched cables.

In addition, electrocardiograph machines are typically large, complex, with many cables, keys and buttons, and thus expensive. Thus, their availability is limited to labs, large and/or well-funded clinical practices, and hospitals.

SUMMARY

One aspect of the disclosure is related to a system configured for performing an electrocardiogram (ECG). Exemplary implementations may enable people with minimal or no training to be able to perform an accurate ECG test. An ECG test, for example may include a 12-lead ECG. One or more implementations of the system may eliminate or greatly reduce many possibilities for human errors, such as incorrect electrode placement, and/or mismatched electrode/cable connections. Implementations of the system may also make an ECG test more standardized for the same human subject, thus making comparing ECG changes over time more precise. The system may include integrated pre-positioned electrodes on an electrode strip, a connector, a data recorder, a connector, peripheral electrodes, a computing platform, and/or other components. The data recorder may include, in exemplary implementations, a compact recorder. The compact recorder, for example, may include a 12-lead ECG recorder. The system described herein may bring simplified, low cost ECGs (e.g., 12-lead ECGs) to smaller and/or non-lab healthcare offices (e.g., pediatrics offices), and may enable subjects to perform ECGs at home. The electrode strip with prepositioned electrodes and a simple snap-in connector may allow optimal ECG testing for adults, children, and/or babies because of the easy and fast electrode placement. In exemplary implementations, the compact recorder provides better performance while reducing cost and size. Thus, the system may provide an affordable ECG testing machine for all clinicians and/or subjects, and may increase the availability and convenience of ECG testing. For example, due to the simplified electrode strip, one snap-in connector, and compact data recorder design, the system may make performing a 12-lead test possible and much easier on special, less cooperative populations (e.g., such as infants and children, patients with psychiatric conditions, and animals).

The electrode strip may include multiple electrodes. The multiple electrodes may be integrated into the electrode strip. In some implementations, for a 12-lead ECG, the electrode strip may include all and/or a portion of the 10 electrodes typically used. Electrode strips having different numbers of electrodes are contemplated and are within the scope of the disclosure. By way of non-limiting example, seven electrodes may be integrated into the electrode strip. In some implementations, corresponding electrode wires may be integrated into the electrode strip. The individual ones of the multiple electrodes may be configured to provide signals conveying information associated with electrocardiograms. The electrodes may be positioned on the electrode strip to align with one or more desired anatomical locations on a human subject.

In some implementations, the electrode strip may include a printed circuit board. The electrodes may be integrated into the printed circuit board. The corresponding wires may include traces within the printed circuit board. In some implementations, the printed circuit board may be flexible.

In some implementations, the electrode strip may include one or more layers of foam. A layer of foam may be hypoallergenic. The layers of foam may include a first layer of foam, a second layer of foam, and/or other layers of foam. The printed circuit board may be disposed in between the first layer of foam and the second layer of foam. In some implementations, the first layer of foam may be configured to face toward the skin of the human subject responsive to the electrode strip being applied to the skin of the human subject. The first layer of foam may include one or more cutouts corresponding to one or more positions of one or more electrodes on the electrode strip. In some implementations, a hydrogel (e.g., a standard Ag/AgCl hydrogel) and/or other conducting material may be disposed within the one or more cutouts.

In some implementations, the system may include one or more peripheral electrodes. The peripheral electrodes may be coupled with the electrode strip via one or more peripheral electrode wires. The one or more peripheral electrodes may be extendable from the electrode strip via the one or more peripheral electrode wires. In some implementations individual peripheral electrode wires may be retractable. In some implementations for a 12-lead ECG, one or more of the ten electrodes required may include peripheral electrodes. By way of non-limiting example, the ten electrodes for a standard clinical 12-lead ECG may include three peripheral electrodes (e.g., RA, LA, LL, and/or other peripheral electrodes), and seven of the ten electrodes may be integrated into the electrode strip. In some implementations, the one or more peripheral electrode wires may include a first section, a second section, and/or other sections. The first section may be external to the electrode strip. The second section may be integrated into the electrode strip.

In some implementations, the electrode strip may include one or more placement indicators. The one or more placement indicators may convey a position at which to apply the electrode strip on the human subject. In some implementations, the placement indicators may include a first placement indicator on a first portion of the electrode strip. The first placement indicator may convey alignment of the first portion of the electrode strip with a breastbone (i.e., sternum) of the human subject. The second placement indicator may convey alignment of the electrode strip at the level of the nipples (which is typically at the fourth intercostal space) of the human subject.

The system may include a data recorder. The data recorder may be configured to receive and record information associated with electrocardiograms. The information associated with electrocardiograms may include the signals provided by the multiple electrodes. In some implementations, the data recorder may include a receiving portion. The receiving portion may be configured to receive a connector to facilitate coupling of the electrode strip with the data recorder. Responsive to the receiving portion of the data recorder receiving a connector integrated with the electrode strip, the data recorder may be removably coupled with the electrode strip.

In some implementations, the data recorder may include a power button, one or more indicator lights, and/or other components. The one or more indicator lights may be configured to provide a status of the electrocardiogram and/or the data recorder. In some implementations, the data recorder may be configured to transmit the electrocardiogram data to one or more computing platforms (e.g., via a wireless transmission, a USB port, a micro-USB port, a cord, and/or other transmission methods).

The system may include a connector. The connector may be disposed at the electrode strip. The connector may be integrated with the electrode strip. The connector may be configured to removably couple the data recorder with the electrode strip via a cableless connection. As such, in some implementations, there may not be a cable between the data recorder and the electrode strip. The connector may include a convergence of the electrode wires. In some implementations, the connector may include the convergence of one or more second sections of the one or more peripheral electrode wires. Responsive to the connector being removably coupled with the data recorder, the data recorder may receive signals from the electrodes via the connector.

Without requiring a cable in between the data recorder and the electrode strip, the data recorder may be disposed proximate to the electrode strip when the system is in use. In some implementations, the cableless connection provided by the connector may eliminate uncomfortable cables that may become entangled, minimize artifacts caused by movements of the subject or the cables, eliminate the possibility of mismatched cable connections, save time in matching the cables with individual electrodes, and/or provide other advantages. In some implementations, the data recorder may be a compact data recorder. For example, the data recorder may have a dimension including one or more of a length of less than six centimeters (cm), a width of less than six centimeters, and/or a thickness of less than two centimeters. As such, the system may provide a portable ECG system including a compact recorder that may be coupled directly to the electrode strip via the connector.

In some implementations, the electrode strip may include a stiffening board. The stiffening board may be disposed proximate to the connector. The stiffening board may facilitate a rigid attachment between the connector and the electrode strip.

These and other features, and characteristics of the present technology, as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
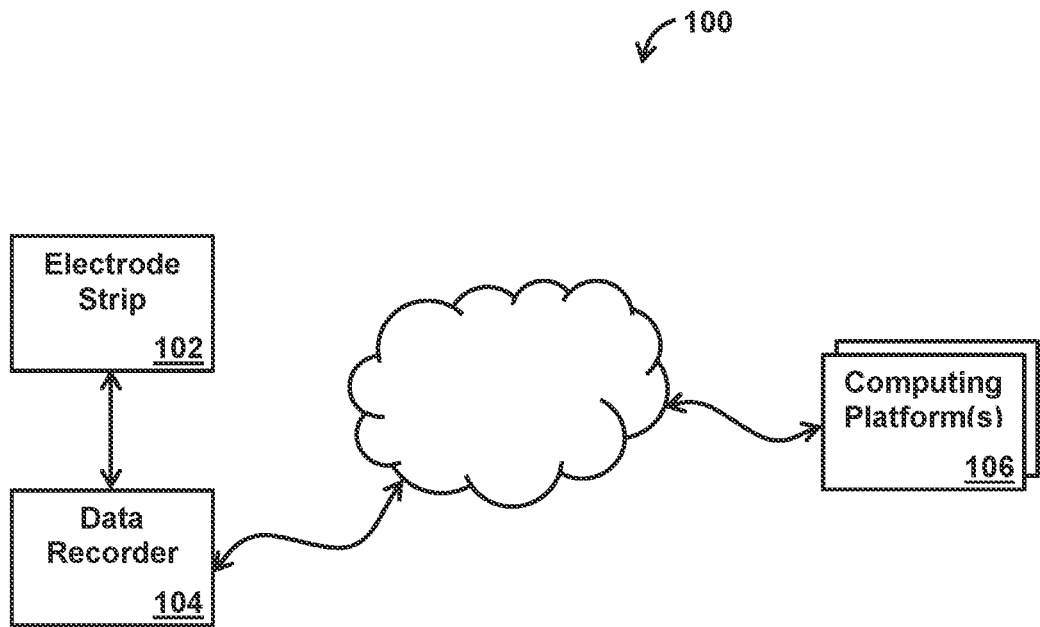
FIG. 1 illustrates a system for performing an electrocardiogram, in accordance with one or more implementations.

FIG. 1 illustrates a system 100 configured for performing an electrocardiogram, in accordance with one or more implementations. System 100 may include one or more of an electrode strip 102, a data recorder 104, computing platform(s) 106, and/or other components. Electrode strip 102 may include multiple electrodes configured to provide signals conveying information associated with electrocardiograms. Data recorder 104 may be configured to receive and record information associated with electrocardiograms. Information associated with electrocardiograms may be communicated from electrode strip 102 to data recorder 104 via a connector. The connector may include a cableless connector. A cableless connector, for example, may include a connector that is configured to connect data recorder 104 with electrode strip 102 without a length of cable between data recorder 104 and electrode strip 102.

In some implementations, the information associated with electrocardiograms may be transmitted to one or more computing platform(s) 106. The one or more computing platform(s) 106 may be configured to receive, process, display, analyze, store, print, wired or wireless transmit, and/or otherwise utilize the information associated with a given electrocardiogram. In some implementations, computing platform(s) 106 may include one or more of a desktop computer, a laptop computer, a handheld computer, a tablet (e.g., an iPad®), a mobile device (e.g., a smartphone), a printer, an ECG system, and/or other computing platforms. In some implementations, the transmission of information associated with electrocardiograms may made wirelessly, via a cord, optical signaling, by a portable storage medium (e.g., a USB drive), and/or via other methods. For example, in some implementations, the wireless transmission may include one or more connection protocols such as, Bluetooth, Bluetooth Low Energy (BLE), radio frequency, WIFI, NFC, WLAN, ZigBee, and/or other connection protocols.

In some implementations, one or more components of system 100 may be operatively linked via one or more electronic communication links. For example, such electronic communication links may be established, at least in part, via Bluetooth and/or other networks/protocols. It will be appreciated that this is not intended to be limiting, and that the scope of this disclosure includes implementations in which one or more components of system 100 may be operatively linked via some other communication media.

In some implementations, electrode strip 102 may be designed for one-time use. The electrode strip 102 may be disposable. The recorded information associated with electrocardiograms may be transmitted (e.g., by wire or wirelessly) and/or transferred (e.g., carried, mailed, and/or otherwise physically moved) by the user to an ECG center for various purposes including one or more of interpretation, transmission to another location, printing, storage, archiving, and/or other purposes. Once the recorded information associated with a given electrocardiogram is delivered to an ECG center, the data recorder may be sterilized, its battery recharged, and/or packaged with a new electrode strip to be ready for another use.

In some implementations, system 100 is configured to be reused for multiple subjects in a clinical setting. The recorded information associated with electrocardiograms may be continuously and/or non-continuously (e.g., via a single post-test transmission) transmitted to a computing platform (e.g., computer, printer, etc.) that may be located within the office. The data recorder may be sanitized at the clinical office for reuse on the next human subject.

While the systems and/or methods described herein refer to example implementations for a human subject, the disclosure is not intended to be limited to human subjects. In some implementations, the systems and methods described herein may be applied to and/or configured for any living subject. By way of a non-limiting example, the systems and methods herein may be applied to and/or configured for animal subjects.

Figure 2:
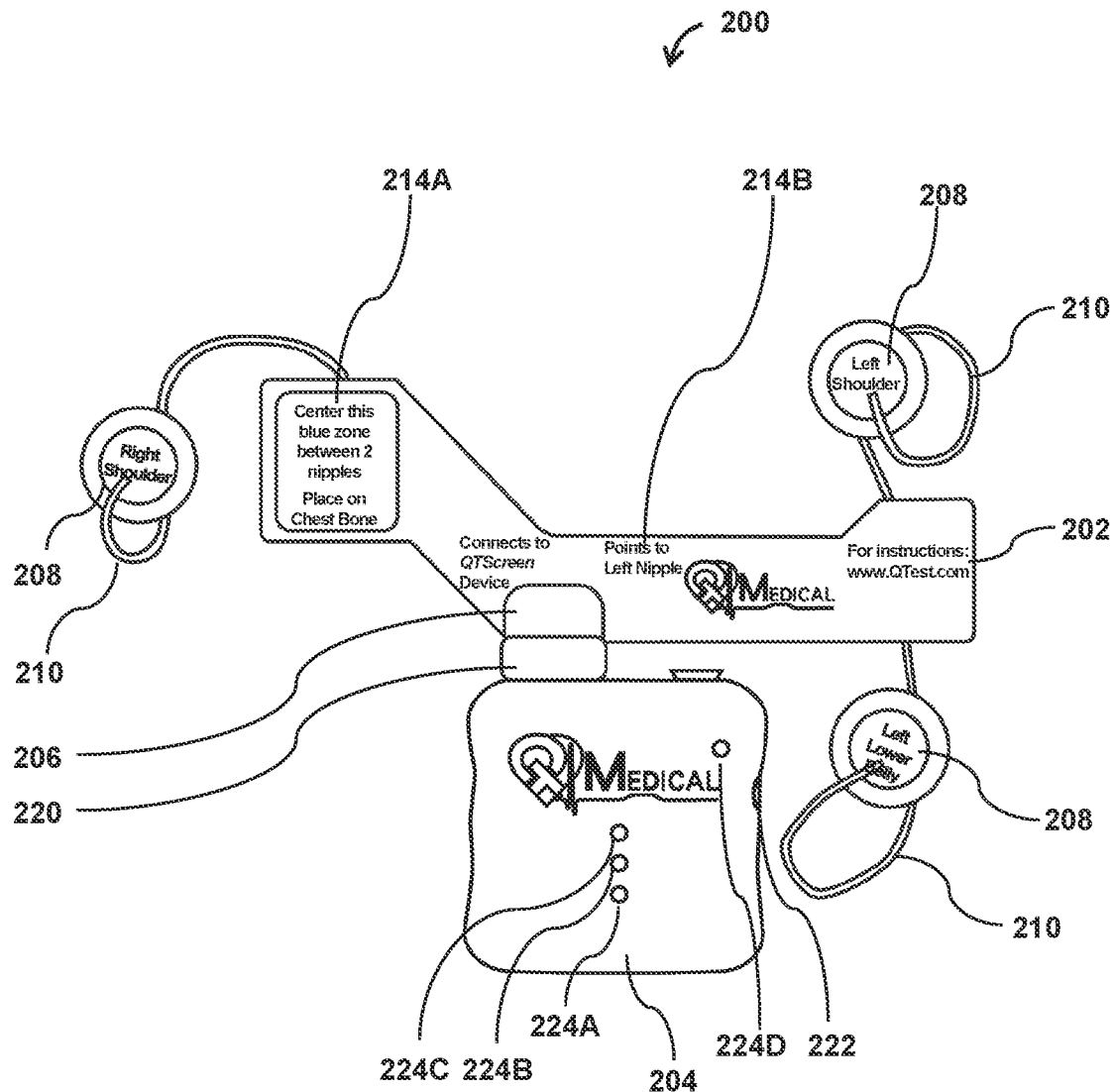
FIG. 2 illustrates a system for performing an electrocardiogram, in accordance with one or more implementations.

FIG. 2 illustrates a system 200 configured for performing an electrocardiogram, in accordance with one or more implementations. System 200 may include one or more components that are the same as or similar to one or more components of system 100. System 200 may include one or more of an electrode strip 202, a data recorder 204, a connector 206, peripheral electrodes 208, peripheral electrode wires 210, placement indicators 214, indicator lights 224, a power button 222, a receiving portion 220, and/or other components. In some implementations, one or more additional components may be included in the system and/or one or more components may be omitted from the system.

Electrode strip 202 may be the same as or similar to electrode strip 102, in some implementations. Electrode strip 202 may include multiple electrodes. Various quantities of electrodes may be used based on the type of ECG performed. The multiple electrodes may be disposed at electrode strip 202. Individual ones of the multiple electrodes may be integrated into electrode strip 202. In some implementations, integrated into electrode strip 202 may include, for example, included in a printed circuit board. The electrode strip 202 may include the printed circuit board.

Electrode strip 202 may include all and/or a portion of the electrodes used for a given ECG. For example, for a 12-lead ECG, seven of the ten electrodes typically used may be integrated into electrode strip 202. Continuing the non-limiting example, the seven electrodes may include six precordial electrodes and a ground electrode. In some implementations, corresponding electrode wires may be integrated into electrode strip 202. The individual ones of the multiple electrodes may be configured to provide signals conveying information associated with electrocardiograms. The electrodes may be positioned on electrode strip 202 to align with one or more desired anatomical locations on a human subject. As such, responsive to a user applying electrode strip 202 to a human subject, a majority of the electrodes may be located in the proper position for performing an ECG.

In some implementations, electrode strip 202 may include one or more placement indicators 214. One or more placement indicators 214 may convey a position at which to apply electrode strip 202 on the human subject. Placement indicators 214 may ensure that the electrodes align with one or more desired anatomical locations on the human subject. By way of non-limiting example, placement indicators 214 may include text, colors, symbols, and/or other content to describe a position at which to apply electrode strip 202.

For example, placement indictors 214 may describe where one or more portions of electrode strip 202 should be aligned; how one or more portions and/or electrode strip 202 should face; a distance from a desired location on a human subject one or more portions and/or electrode strip 202 should be; a level, location and alignment of electrode strip 202 in relation to commonly recognized anatomical landmarks; and/or other information. In some implementations, placement indicators 214 may include a first placement indicator 214A on a first portion of electrode strip 202. The first placement indicator 214A may convey alignment of the first portion of electrode strip 202 with the breastbone of the human subject. In some implementations, placement indicators 214 may include a second placement indicator 214B on a second portion of electrode strip 202. The second placement indicator 214B may convey (e.g., via an arrow) that the second portion should point to the left nipple of the human subject.

In some implementations, some of the electrodes typically used for an ECG may not be integrated into electrode strip 202. For example, system 200 may include one or more peripheral electrodes 208. Peripheral electrodes 208 may be coupled to electrode strip 202 via peripheral electrode wires 210. One or more peripheral electrodes 208 may be extendable from electrode strip 202 via one or more peripheral electrode wires 210. As such, for example, peripheral electrodes 208 may expand the coverage area of electrode strip 202.

In some implementations, a few of the total number of electrodes required for an ECG may include peripheral electrodes. By way of non-limiting example, for a 12-lead ECG, three of the ten electrodes may include peripheral electrodes 208. As such, for example, to perform a 12-lead ECG via system 200, both electrode strip 202 and peripheral electrodes 208 are applied to the subject.

In some implementations, one or more peripheral electrode wires 210 may include a first section, a second section, and/or other sections. The first section may be external to electrode strip 202 (e.g., the first sections of peripheral electrode wires 210 are the only section(s) of peripheral electrode wires 210 visible in the view presented by FIG. 2). The second section may be integrated into electrode strip 202 (e.g., not visible in the view presented by FIG. 2). In some implementations, electrode strip 202 may include a printed circuit board. As such, the electrodes may be integrated into the printed circuit board. The corresponding electrode wires may include traces within the printed circuit board. In some implementations, the printed circuit board may be flexible.

In some implementations, electrode strip 102 may at least partially include an adjustable material. The adjustable material may include, for example, a stretchable material, a material including one or more adjustment mechanisms (e.g., a slide, clip, hook and loop mechanism, snaps, and/or other adjustment mechanisms), and/or other adjustable materials. As such, for example, electrode strip 102 may fit human subjects of various sizes. For example, an adjustable and/or stretchable electrode strip may fit various human subjects having chests of different sizes.

In some implementations, electrode strip 202 may include one or more layers of foam. The foam may include a soft, stretchable, hypoallergenic, and/or otherwise biocompatible foam. The layers of foam may include a first layer of foam, a second layer of foam, and/or other layers of foam. The layers of foam may include the same and/or different types of foam. In some implementations, the printed circuit board may be disposed in between the first layer of foam and the second layer of foam. In some implementations, the first layer of foam may be configured to face toward the skin of the human subject responsive to electrode strip 202 being applied to the skin of the human subject. The first layer of foam may include one or more cutouts corresponding to one or more positions of one or more electrodes on electrode strip 202. In some implementations, a hydrogel material may be disposed within the one or more cutouts.

System 200 may include data recorder 204. Data recorder 204 may be the same as or similar to recorder 104, in some implementations. The data recorder may be configured to receive and record information associated with electrocardiograms. In some implementations, data recorder 204 may be configured to transmit the information associated with electrocardiograms to one or more computing platforms. The information associated with electrocardiograms may include the signals provided by the multiple electrodes. Data recorder 204 may include one or more of a processor component, integrated ECG analog frontend, a memory component, a communications interface (e.g., a wired and/or a wireless transmission component), a battery, and/or other components. Data recorder 204 may be battery powered and/or chargeable (e.g., via a USB/micro USB, or by inductive charging).

In some implementations, data recorder 204 may only be configured to receive, record, and/or transmit information associated with electrocardiograms. Data recorder 204 may be configured to have enough memory to record information associated with an electrocardiogram at any given time. In some implementations, for example, the narrow functions of data recorder 204 may allow for data recorder 204 to have a compact size, simple operation, and prolonged battery life.

In some implementations, data recorder 204 may be configured by one or more computing platform(s) (e.g., the same as or similar to computing platform(s) 106). In some implementations, patient identifying information may be entered and/or kept by the computing platforms. In some implementations, data recorder 204 may be paired with a computing platform (e.g., and IPad®) including an application. An administrator account of the application may enable a user to configure the data recorder (e.g., such as system information, date and time, data recording rate, wireless transmission, and/or other settings/configurations). By way of a non-limiting use example, the user may be able to use a camera of the computing platform to scan the patient's bar code and/or QR code for identification. By way of another non-limiting use example, the user may be able to type information directly into the computing platform. In some implementations, the application may display the ECG tracing, and/or may be able to record, analyze and/or store data (e.g., the information associated with an electrocardiogram). The user may, for example, be able to transmit the data to a server (e.g., an ECG center), print, or upload to an electronic medical record (e.g., a patient's chart).

In some implementations, data recorder 204 may include a compact data recorder. Data recorder 204 may include a dimension (e.g., length, width, height, diameter, and/or other dimensions) of less than 30 centimeters. In some implementations, data recorder 204 may have one or more dimensions including a length between 1 centimeter and 40 centimeters, a width between 1 centimeter and 40 centimeters, and/or a thickness (e.g., height) between 2 millimeters and 10 centimeters. For example, a data recorder 204 may have dimensions including a length of less than six centimeters, a width of less than six centimeters, and a thickness of less than two centimeters. By way of non-limiting use example, data recorder 204 may have a dimension of one or more of about five centimeters in length, about five centimeters in width, and/or about one centimeter in thickness. By way of another non-limiting use example, data recorder 204 may have a dimension of one or more of about seven centimeters in length, about five centimeters in width, and/or about 1.5 centimeters in thickness. By way of another non-limiting use example, data recorder 204 may have a dimension of one or more of about 10 centimeters in length, about 10 centimeters in width, and/or about two centimeters in thickness.

In some implementations, data recorder 204 may have a weight between a quarter of half ounce and 10 ounces. In a non-limiting use example, data recorder 204 may include a weight of about 1 ounce. In some implementations, data recorder 204 may include various shapes and/or sizes that have a footprint smaller than or equal to the example dimensions provided herein. In some implementations, data recorder 204 may include a data recorder with additional functions beyond receiving, recording, and/or transmitting information associated with electrocardiograms.

In some implementations, data recorder 204 may include receiving portion 220. Receiving portion 220 may be configured to receive a connector 206. Receiving portion 220 may be configured to receive a connector 206 to facilitate coupling of electrode strip 202 with data recorder 204. Responsive to receiving portion 220 receiving connector 206, wherein connector 206 is integrated with electrode strip 202, data recorder 204 may be removably coupled with electrode strip 202. Removably coupled may include coupled with in such a way that de-coupling and/or re-coupling may occur one or more times.

In some implementations, data recorder 204 may include power button 222, one or more indicator lights 224, and/or other components. The one or more indicator lights may be configured to provide a status of a given electrocardiogram and/or data recorder 204. The status of a given electrocardiogram may include one or more of an ECG status (e.g., whether an ECG is currently being conducted), a completion status, a time status, and/or other statuses. The status of data recorder 204 may include one or more of a power status (e.g., whether the data recorder is on), a battery status, a recording/receiving status (e.g., whether the data recorder is recording and/or receiving information), a pairing status (e.g., whether the electrodes are coupled to the data recorder), an electrode status (e.g., whether signals are being received from one or more electrodes), and/or other statuses. In some implementations, recorder 204 may be configured to transmit the electrocardiogram data to one or more computing platforms (e.g., via a wireless transmission, a USB port, a cord, and/or other transmission methods).

In some implementations, data recorder 204 may include a display. The display may include a small screen (e.g., LED, LCD, and/or other types of screens) to display one or more statuses. The one or more statuses to be displayed may include one or more of the status of data recorder 204, and/or the status of an electrocardiogram. By way of non-limiting use example, a status related to one or more of power, Bluetooth pairing, electrode attachment to skin (leads off detection), data recording, and/or other functions/features may be displayed.

System 200 may include connector 206. Connector 206 may be disposed at electrode strip 202. Connector 206 may be integrated with electrode strip 202. Connector 206 may be configured to removably couple data recorder 204 with electrode strip 202 via a cableless connection. A cableless connection may include a connection that does not require a cable disposed between electrode strip 202 and data recorder 204. For example, connector 206 may include a male connector portion that is configured to couple with a female connector portion disposed at data recorder 204. As such, in some implementations, there may not be a cable and/or a set of cables between data recorder 204 and electrode strip 202.

Connector 206 may include a convergence of the electrode wires. A convergence may describe a location at which multiple electrode wires approach each other and/or a connection region. For example, a convergence may include a gathering of at least portions of one or more electrode wires to be included in a connector (e.g., connector 206). Connector 206 may include a convergence of both the electrode wires corresponding with the integrated electrodes and/or the second sections of peripheral electrode wires 210, corresponding with peripheral electrodes 208. The electrode wires may be located at specific positions within the convergence of the electrode wires. Thus, responsive to connector 206 being removably coupled with a corresponding receiving portion (e.g., a female connector portion on data recorder 204), the electrode wires may automatically be aligned to ensure the proper electrode wire matches with the corresponding port. As such, an operator may only have to facilitate one connection by coupling connector 206 to data recorder 204. In some implementations, connector 206 may be configured such that it may only couple with (e.g., fit together seamlessly) data recorder 204 in one direction to ensure the proper alignment of electrode wires. Responsive to connector 206 being removably coupled with data recorder 204, data recorder 204 may be configured to receive signals from the electrodes via connector 206.

In some implementations, electrode strip 202 may include a stiffening board. The stiffening board may be disposed proximate to connector 206. As such, the stiffening board may facilitate a rigid attachment between connector 206 and electrode strip 202. By way of non-limiting example, the stiffening board may be at least partially disposed at the convergence of the electrode wires.

In some implementations, wherein connector 206 includes a cableless configuration, recorder 204 may be disposed proximate to electrode strip 202 when connector 206 is coupled with data recorder 204. Thus, it may be advantageous for data recorder 204 to have a compact configuration such that system 200 may provide a portable ECG system without cables that may be bulky, uncomfortable, and/or inconvenient.

Figure 3:
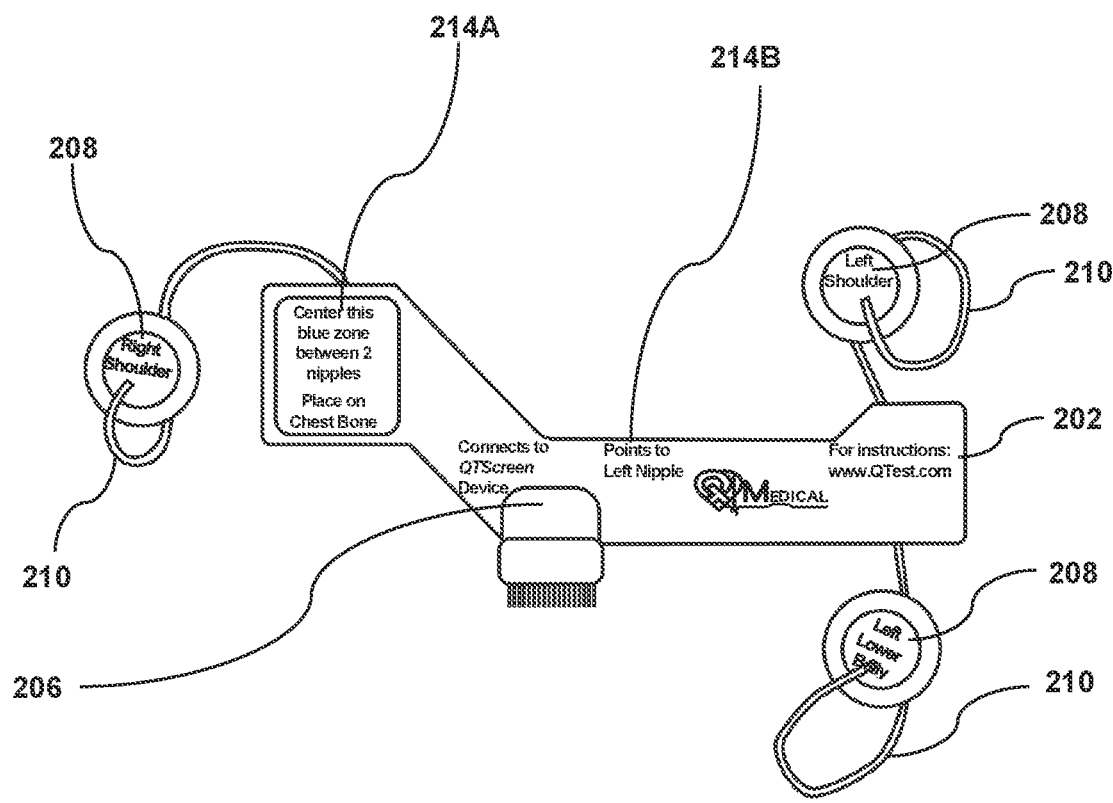
FIG. 3 illustrates a front view of an electrode strip, in accordance with one or more implementations.
Figure 4:
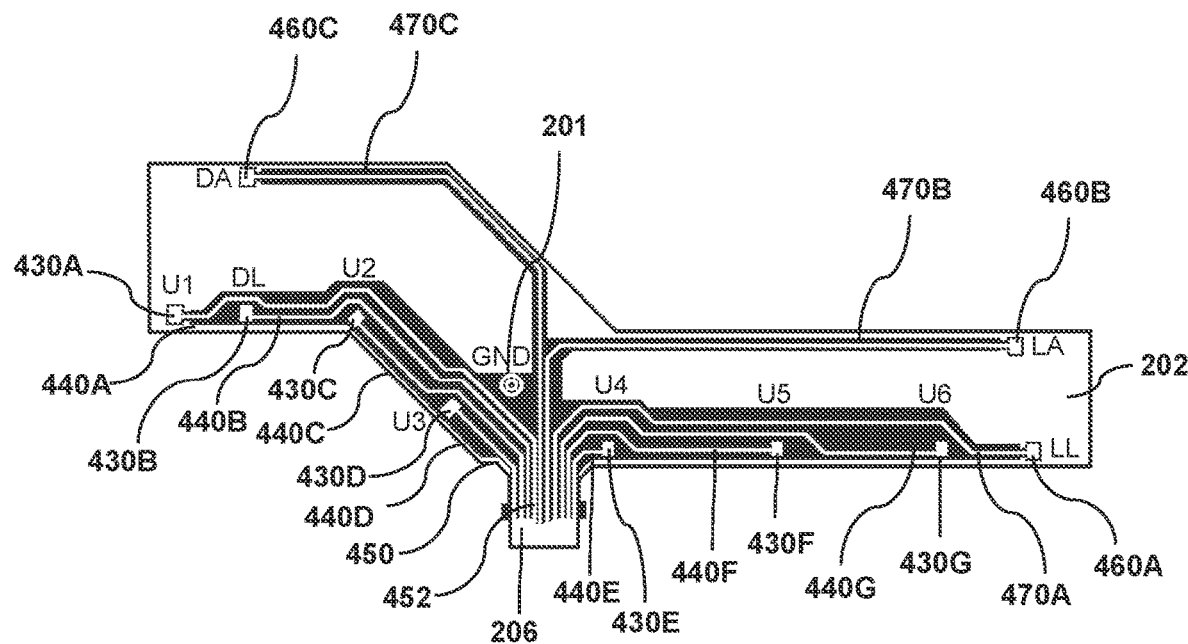
FIG. 4 illustrates a printed circuit board of an electrode strip, in accordance with one or more implementations.

FIG. 3 and FIG. 4 illustrate a front view of an electrode strip and a printed circuit board of an electrode strip respectively, in accordance with one or more implementations. The electrode strip illustrated in FIG. 3 and FIG. 4 may include electrode strip 202. In some implementations, as illustrated in FIG. 3, connector 206 may include a male connector portion. The male connector portion may be configured to fit (e.g., removably couple with) seamlessly with a corresponding female connector portion (e.g., not illustrated in FIG. 3). In some implementations, connector 206 may include one or more of an HDMI connector, a USB connector, a micro-USB connector, a mini-USB connector, a serial bus connector, a Lightening connector, a proprietary connector, and/or other types of connectors.

As illustrated by FIG. 4, electrode strip 202 may include a printed circuit board 201. Printed circuit board 201 may include one or more integrated electrodes 430. In some implementations, printed circuit board 201 may include corresponding electrode wires 440. Corresponding electrode wires 440 may include traces within printed circuit board 201. In some implementations, electrode strip 202 may include one or more connection points 460 for one or more peripheral electrodes 208.

In some implementations, electrode strip 202 may include one or more peripheral wires 210. Printed circuit board 201 may include one or more second sections 470 of peripheral wires 210. Second sections 470 may be integrated into printed circuit board 201. For example, second sections 470 may be included in printed circuit board 201 as traces. In some implementations, a given peripheral electrode wire 210 may be continuous between a given first section and a given second section. In some implementations, there may be one or more electrical connections between the given first section and the given second section of the given peripheral electrode wire 210. As such, in some implementations, at least a portion of peripheral electrode wires 210 may be able to be connected to and/or disconnected from electrode strip 202.

In some implementations, connector 206 may include a convergence 452 of one or more of: electrode wires 440; second sections 470; and/or other electrode wires. In some implementations, convergence 452 may be included in printed circuit board 201. For example, convergence 452 may be included in printed circuit board 201 as a convergence of traces corresponding to the electrode wires and/or second sections.

In some implementations, printed circuit board 201 may be flexible. In some implementations, electrode strip 202 may include a stiffening board 450. Stiffening board 450 may include a rigid material such as a plastic, a metal, a composite material, glass, and/or other rigid materials. Stiffening board 450 may be disposed proximate to connector 206. Stiffening board 450 may be layered on top, below, and/or in between at least a portion of one or more of electrode strip 202, printed circuit board 201, connector 206, one or more layers of foam, and/or other components. As such, the stiffening board may facilitate a rigid attachment between connector 206 and electrode strip 202. By way of non-limiting example, the stiffening board may be at least partially disposed at the convergence of the electrode wires.

Figure 5:
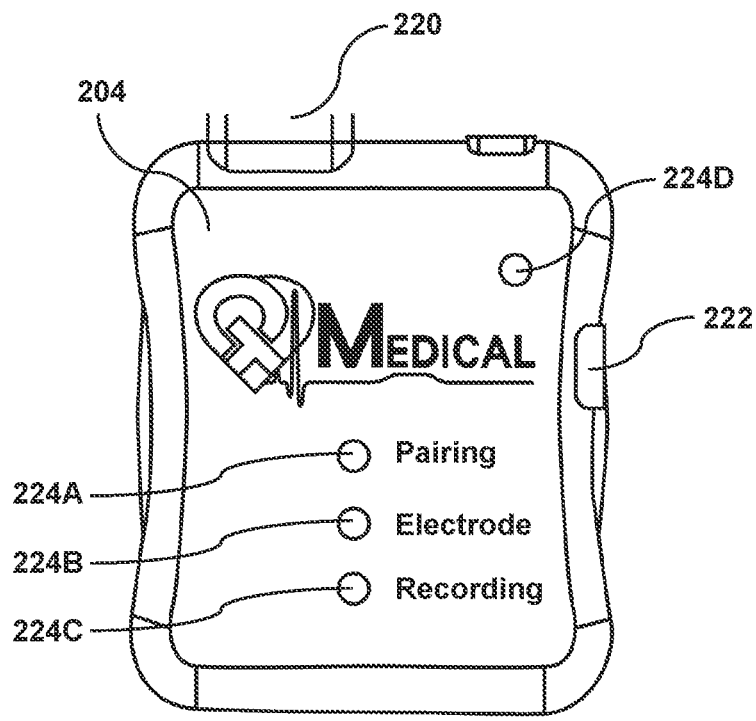
FIG. 5 illustrates a recorder, in accordance with one or more implementations.

FIG. 5 illustrates a data recorder, in accordance with one or more implementations. The data recorder illustrated in FIG. 5 may include data recorder 204. Data recorder 204 may include one or more of: indicator lights 224; power button 222; receiving portion 220; and/or other components. Power button 222 may be configured to activate data recorder 204 in order to begin recording information associated with an electrocardiogram. In some implementations, indicator lights 224 may correspond to specific status indications. Indicator light 224A may, for example, correspond to a pairing status. Indicator light 224B may correspond to an electrode status. Indicator light 224C may, for example, correspond to a recording status. Indicator light 224D may, for example, correspond to a power status.

In some implementations, data recorder 204 may include receiving portion 220 for receiving a connector. Receiving portion 220 may be configured to receive connector 206 (see FIG. 2, FIG. 3, and FIG. 4). Receiving portion 220 may be configured to receive connector 206 to facilitate the coupling of electrode strip 202 with data recorder 204. Responsive to receiving portion 220 receiving connector 206, wherein connector 206 is integrated with electrode strip 202, data recorder 204 may be removably coupled with electrode strip 202.

Figure 6:
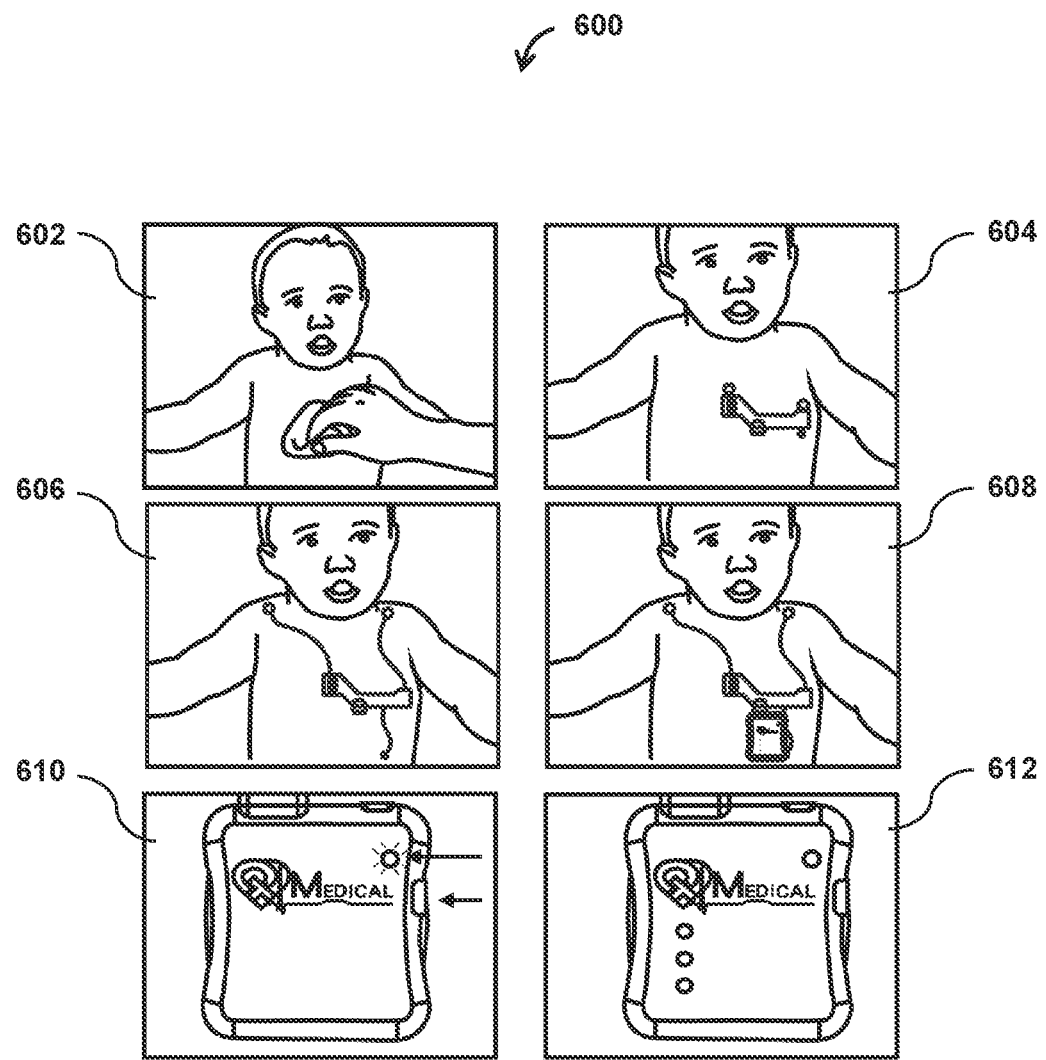
FIG. 6 illustrates a method for performing an electrocardiogram, in accordance with one or more implementations.

FIG. 6 illustrates a method 600 for performing an electrocardiogram, in accordance with one or more implementations. The method depicted in FIG. 6 is described in greater detail herein. The described operations may be accomplished using some or all of the system components described in detail herein and, in some implementations, various operations may be performed in different sequences and various operations may be omitted. Additional operations may be performed along with some or all of the operations shown in the depicted method steps. One or more steps may be performed simultaneously. Accordingly, the operations as illustrated (and described in greater detail below) are exemplary by nature and, as such, should not be viewed as limiting. The method may be performed by a user including one or more of a caregiver, a relative, a friend, a medical practitioner, a subject him/herself, and/or other users.

In some implementations, at operation 602, a user may clean the skin of a human subject to ensure the skin is clean and dry. At operation 604, a user may remove a plastic cover on an electrode strip to expose one or more sticky patches (e.g., hydrogel material and/or other sticky material) on the electrode strip. The electrode strip may be applied to the chest of the human subject. In some implementations, a first placement indicator may convey alignment of a first portion (e.g., a blue portion) of the electrode strip with the breastbone of the human subject. A second placement indicator may convey a second portion (e.g., including an arrow) that should point to the left nipple of the human subject. The electrode strip in operation 604 may be the same as or similar to electrode strip 202. The first placement indicator in operation 604 may be the same as or similar to first placement indicator 214A. The second placement indicator in operation 604 may be the same as or similar to second placement indicator 214B.

At operation 606, one or more peripheral electrodes may be pulled to extend the peripheral electrodes away from the electrode strip. A first peripheral electrode (e.g., including a white placement indicator), may be applied to the right shoulder of the human subject. A second peripheral electrode (e.g., including a red placement indicator), may be applied to the left shoulder of the human subject. A third peripheral electrode (e.g., including a blue placement indicator), may be applied to the left lower belly of the human subject. The one or more peripheral electrodes included in operation 606 may be the same as or similar to peripheral electrodes 208.

At operation 608, a data recorder may be connected to the electrode strip via a connector. The data recorder included in operation 608 may be the same as or similar to data recorder 204. The connector included in operation 608 may be the same as or similar to connector 206. At operation 610, a user may activate the data recorder by pushing a power button on the data recorder. Responsive to activating the data recorder, a power status indicator light may light up (e.g., as a red light). The power button included in operation 610 may be the same as or similar to power button 222. The power status indicator light included in operation 610 may be the same as or similar to indicator light 224D.

At operation 612, three indicator lights on the data recorder may light up (e.g., as green lights) to indicate the data recorder is receiving and recording information associated with the electrocardiogram. After an amount of time (e.g., 10 minutes) the indicator lights may change color (e.g., to amber) to indicate the data recorder has stopped receiving and recording information associated with the electrocardiogram. The three indicator lights included in operation 612 may be the same as or similar to indicator lights 224.

Figure 7:
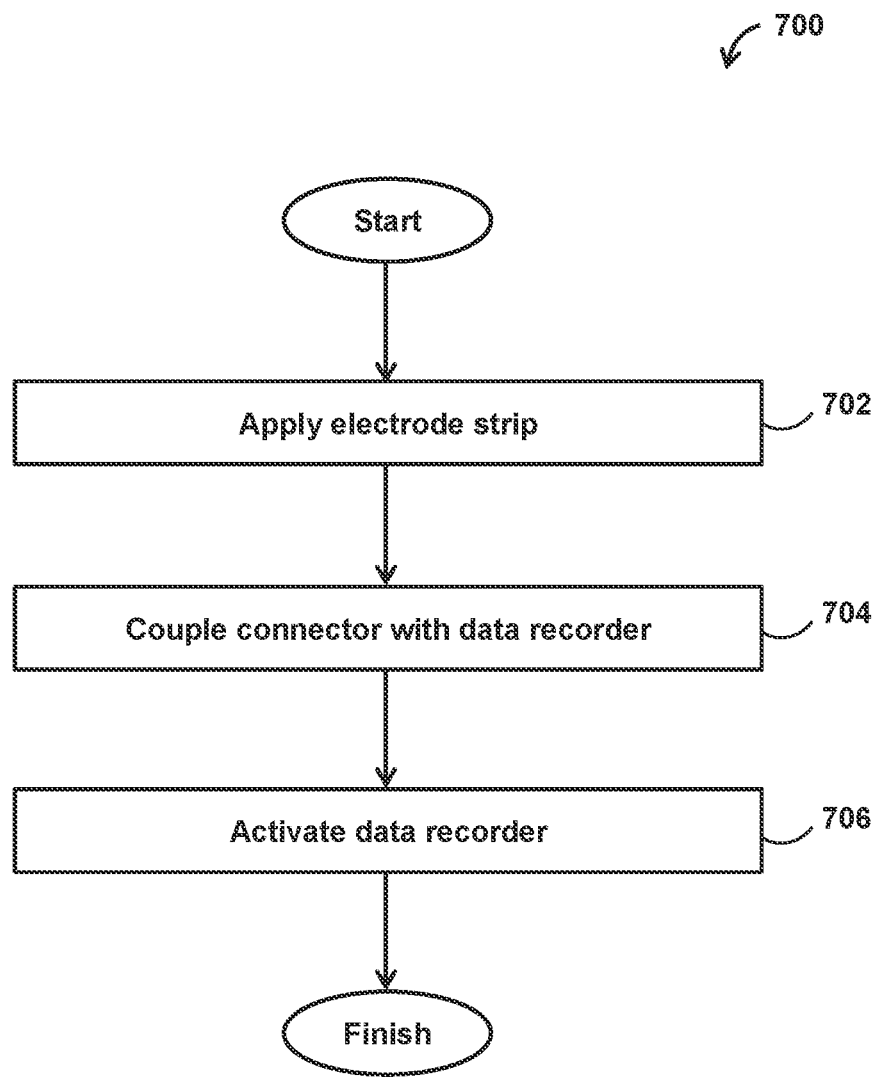
FIG. 7 illustrates a method for performing an electrocardiogram, in accordance with one or more implementations.

FIG. 7 illustrates a method 700 for performing an electrocardiogram, in accordance with one or more implementations. The method depicted in FIG. 7 is described in greater detail herein. The described operations may be accomplished using some or all of the system components described in detail herein and, in some implementations, various operations may be performed in different sequences and various operations may be omitted. Additional operations may be performed along with some or all of the operations shown in the method steps. One or more steps may be performed simultaneously. Accordingly, the operations as illustrated (and described in greater detail below) are exemplary by nature and, as such, should not be viewed as limiting. The method may be performed by a user including one or more of a caregiver, a relative, a friend, a medical practitioner, and/or other users.

At operation 702, an electrode strip may be applied to an area of skin on a human subject. The electrode strip may include multiple electrodes and corresponding electrode wires integrated into the electrode strip. Individual ones of the multiple electrodes may be configured to provide signals conveying information associated with electrocardiograms. The electrodes may be positioned on the electrode strip to align with one or more desired anatomical locations on a human subject. The electrode strip in operation 702 may be the same as or similar to electrode strip 202.

At operation 704, a connector may be coupled with a data recorder. The connector may be disposed at and integrated with the electrode strip. The connector may be coupled with the data recorder via a cableless connection. The data recorder may be configured to receive and record information associated with electrocardiograms. The connector may include a convergence of the electrode wires. As such, responsive to the connector being coupled with the data recorder, the data recorder may receive signals from the electrodes via the connector. The connector in operation 704 may be the same as or similar to connector 206. The data recorder in operation 704 may be the same as or similar to data recorder 204.

At operation 706, the data recorder may be activated. Once activated, the data recorder may begin receiving and recording information associated with an electrocardiogram. The data recorder in operation 706 may be the same as or similar to data recorder 204.

Figure 8:
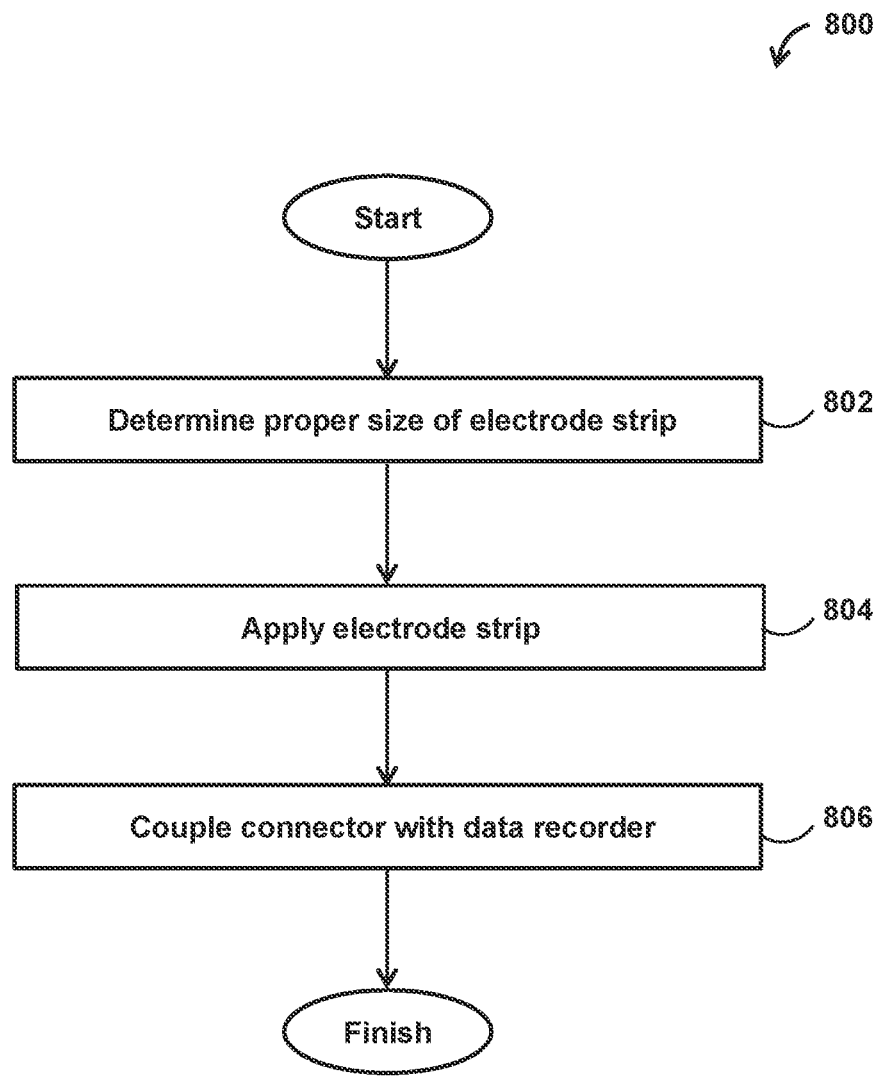
FIG. 8 illustrates a method for performing an electrocardiogram, in accordance with one or more implementations.

FIG. 8 illustrates a method 800 for performing an electrocardiogram, in accordance with one or more implementations. The method depicted in FIG. 8 is described in greater detail herein. The described operations may be accomplished using some or all of the system components described in detail herein and, in some implementations, various operations may be performed in different sequences and various operations may be omitted. Additional operations may be performed along with some or all of the operations shown in the method steps. One or more steps may be performed simultaneously. Accordingly, the operations as illustrated (and described in greater detail below) are exemplary by nature and, as such, should not be viewed as limiting. The method may be performed by a user including one or more of a caregiver, a relative, a friend, a medical practitioner, and/or other users.

At operation 802 a proper size of an electrode strip may be determined. The electrode strip may include multiple electrodes and corresponding electrode wires integrated into the electrode strip. The individual ones of the multiple electrodes may be configured to provide signals conveying information associated with electrocardiograms. The electrodes may be positioned on the electrode strip such that responsive to determining the proper size for a human subject, the electrodes align with one or more desired anatomical locations on the human subject.

The proper size of the electrode strip may be determined based on an algorithm and/or a corresponding physical characteristic of the human subject. In some implementations, the algorithm may include one or more physical characteristics describing the human subject. The physical characteristics describing the human subject may include one or more of a shirt size typically worn by the human subject, a body-mass index of the human subject, a chest circumference of the human subject, a shoulder breadth of the human subject, a height of the human subject, a weight of the human subject, a sex of the human subject, an age of the human subject, and/or other characteristics describing the human subject and/or the body size and shape of the human subject. By way of non-limiting example, the algorithm may include 0.3 times (e.g., 30%) the chest circumference of the human subject, wherein the chest circumference is measured at the nipple line. The electrode strip in operation 802 may be the same as or similar to electrode strip 202.

At operation 804, the electrode strip may be applied to the skin of the human subject. The electrode strip may be applied based on one or more placement indicators included on the electrode strip. The electrode strip in operation 804 may be the same as or similar to electrode strip 202.

At operation 806, a connector may be coupled with a data recorder. The connector may be disposed at and integrated with the electrode strip. The connector may be coupled with the data recorder via a cableless connection. The data recorder may be configured to receive and record information associated with electrocardiograms. The connector may include a convergence of the electrode wires. As such, responsive to the connector being coupled with the data recorder, the data recorder may receive signals from the electrodes via the connector. The connector in operation 804 may be the same as or similar to connector 206. The data recorder in operation 804 may be the same as or similar to data recorder 204.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system for performing an electrocardiogram, the system comprising:
    an electrode strip comprising:
        a flexible printed circuit board including multiple integrated electrodes and corresponding electrode wires integrated into the electrode strip, individual ones of the multiple integrated electrodes being configured to provide signals conveying information associated with electrocardiograms, the integrated electrodes being positioned on the electrode strip to align with one or more desired anatomical locations on a human subject;
        three peripheral electrodes, RA (right arm), LA (left arm), and LL (left leg), which are electrically connected to the electrode strip via peripheral electrode wires, the peripheral electrode wires allowing each of the three individual peripheral electrodes to be pulled to a respective appropriate position for the electrocardiogram, wherein the RA peripheral electrode is configured to be pulled and placed proximate to a right arm of the human subject distal to a right shoulder joint; the LA peripheral electrode is configured to be pulled and placed proximate to a left arm of the human subject distal to a left shoulder joint; and the peripheral LL electrode is configured to be pulled and placed on a left side of the human subject distal to a left hip joint; and
        a ground (GND) electrode located on the electrode strip, and not configured to be pulled to an external location,
        wherein the electrode strip includes:
            a horizontally extending first portion that includes a first textual, shape, and/or color placement indicator conveying that the first portion is configured to be placed on a sternum of the human subject centered between nipples of the human subject;
            a second portion coupled to the first portion, the second portion declining at an angle relative to the first portion and connecting the first portion to a horizontally extending third portion, the third portion configured to extend below a left nipple of the human subject as a result of the declining of the second portion, the third portion including a second textual, shape, and/or color placement indicator conveying that a specific location on the third portion should point to the left nipple;
    a data recorder configured to receive, record, and transmit, information associated with electrocardiograms, wherein the data recorder includes a housing, a processor, an integrated ECG analog frontend, a memory, a communications interface, a battery, a power button, and indicator lights, wherein the housing includes the processor, the integrated ECG analog frontend, the memory, the communications interface, the battery, the power button, and the indicator lights, and has a length of less than 8 centimeters, a width of less than 8 centimeters, a thickness of less than 2 centimeters, and a weight of 1-10 ounces,
    wherein the indicator lights are configured to provide a status of the electrocardiogram and the data recorder, the indicator lights comprise a power indicator light configured to indicate whether the data recorder is on, a pairing indicator light configured to indicate whether one or more of the integrated and/or peripheral electrodes are coupled to the data recorder, and a recording indicator light configured to indicate whether the data recorder is recording information and at least two of the indicator lights are arranged in a row on a surface of the housing such that the indicator lights are visible when the housing is positioned on the human subject; and a connector disposed at and integrated with the electrode strip, the connector being configured to removably couple the data recorder with the electrode strip via a cableless connection the connector including a convergence of the electrode wires such that responsive to the connector being removably coupled with the data recorder, the data recorder receives signals from the integrated and/or peripheral electrodes via the connector, the connector being located at a transition between the second portion and the third portion of the electrode strip, wherein the electrode strip includes a stiffening board, the stiffening board disposed proximate to the connector and at least partially at the convergence of the electrode wires, the stiffening board being layered on top, below, and/or in between at least a portion of the electrode strip and/or the flexible printed circuit board, the stiffening board facilitating a rigid attachment between the connector and the electrode strip.

2. The system of claim 1, wherein the electrode strip includes the flexible printed circuit board such that the integrated electrodes are integrated into the flexible printed circuit board and the corresponding electrode wires include traces within the flexible printed circuit board.

3. The system of claim 2, wherein the electrode strip includes a stretchable material such that it is configured to fit human subjects of varying size.

4. The system of claim 2, wherein the electrode strip includes:
a first layer of foam configured to contact skin on the human subject and including multiple cutouts and hydrogels, wherein the cutouts are spacedly disposed in the first layer of foam, and the hydrogels are disposed in the cutouts; and
a second layer of foam,
wherein the flexible printed circuit board is disposed between the first layer of foam and the second layer of foam.

5. The system of claim 4, wherein the integrated electrodes are positioned corresponding to the cutouts of the first layer of foam and are in contact with the hydrogels in the cutouts.

6. The system of claim 1, wherein the peripheral electrode wires each include a first section and a second section, the first section being external to the electrode strip and the second section being integrated into the electrode strip such that the connector includes a convergence of one or more second sections of the one or more peripheral electrode wires.

7. The system of claim 1, wherein the data recorder has a length of less than 6 centimeters, and a width of less than 6 centimeters.

8. The system of claim 1, wherein the data recorder includes a display, the display being configured to provide a status of one or both of the electrocardiogram or the data recorder.

9. The system of claim 1, wherein the data recorder is configured to transmit electrocardiogram data to one or more computing platforms.

10. The system of claim 9, wherein the data recorder is configured to wirelessly transmit the electrocardiogram data to the one or more computing platforms.

11. The system of claim 1, wherein the peripheral electrode wires are adjustable and long enough to allow each of the three individual peripheral electrodes to be pulled to the respective appropriate position for the electrocardiogram, thus meeting applicable standard 12-lead ECG measurement requirements.

12. The system of claim 1, wherein the peripheral electrode wires are disposed at the electrode strip before being pulled to the respective appropriate position for the electrocardiogram.

13. A method for performing an electrocardiogram, the method comprising:
applying an electrode strip to an area of skin on a human subject, the electrode strip comprising:
a flexible printed circuit board including multiple integrated electrodes and corresponding electrode wires integrated into the electrode strip, individual ones of the multiple integrated electrodes being configured to provide signals conveying information associated with electrocardiograms, the integrated electrodes being positioned on the electrode strip to align with one or more desired anatomical locations on the human subject;
three peripheral electrodes, RA (right arm), LA (left arm), and LL (left leg), which are electrically connected to the electrode strip via peripheral electrode wires, the peripheral electrode wires allowing each of the three individual peripheral electrodes to be pulled to a respective appropriate position for the electrocardiogram, wherein the RA peripheral electrode is configured to be pulled and placed proximate to a right arm of the human subject distal to a right shoulder joint; the LA peripheral electrode is configured to be pulled and placed proximate to a left arm of the human subject distal to a left shoulder joint; and the peripheral LL electrode is configured to be pulled and placed on a left side of the human subject distal to a left hip joint; and
a ground (GND) electrode located on the electrode strip, and not configured to be pulled to an external location,
wherein the electrode strip includes:
a horizontally extending first portion that includes a first textual, shape, and/or color placement indicator conveying that the first portion is configured to be placed on a sternum of the human subject centered between nipples of the human subject;
a second portion coupled to the first portion, the second portion declining at an angle relative to the first portion and connecting the first portion to a horizontally extending third portion, the third portion configured to extend below a left nipple of the human subject as a result of the declining of the second portion, the third portion including a second textual, shape, and/or color placement indicator conveying that a specific location on the third portion should point to the left nipple; and
coupling a connector disposed at and integrated with the electrode strip at a transition between the second portion and the third portion of the electrode strip with a data recorder via a cableless connection, wherein:
the connector includes a convergence of the electrode wires such that responsive to the connector being coupled with the data recorder, the data recorder receives signals from the electrodes via the connector, the data recorder is configured to receive, record, and transmit, information associated with electrocardiograms, the data recorder includes a housing, a processor, an integrated ECG analog frontend, a memory, a communications interface, a battery, a power button, and indicator lights, the indicator lights being configured to provide a status of the electrocardiogram and the data recorder, the indicator lights comprising a power indicator light configured to indicate whether the data recorder is on, a pairing indicator light configured to indicate whether one or more of the integrated and/or peripheral electrodes are coupled to the data recorder, and a recording indicator light configured to indicate whether the data recorder is recording information, at least two of the indicator lights being arranged in a row on a surface of the housing such that the indicator lights are visible when the housing is positioned on the human subject, the housing includes the processor, the integrated ECG analog frontend, the memory, the communications interface, the battery, the power button, and the indicator lights, and has a length of less than 8 centimeters, a width of less than 8 centimeters, a thickness of less than 2 centimeters, and a weight of 1-10 ounces; and activating the data recorder to begin receiving and recording information associated with an electrocardiogram, wherein the electrode strip includes a stiffening board, the stiffening board disposed proximate to the connector and at least partially at the convergence of the electrode wires, the stiffening board being layered on top, below, and/or in between at least a portion of the electrode strip and/or the flexible printed circuit board, the stiffening board facilitating a rigid attachment between the connector and the electrode strip.

14. The method of claim 13, wherein the electrode strip includes the flexible printed circuit board such that the integrated electrodes are integrated into the flexible printed circuit board and the corresponding electrode wires include traces within the flexible printed circuit board.

15. The method of claim 14, wherein the electrode strip includes a stretchable material such that it is configured to fit human subjects of varying size.

16. The method of claim 14, wherein the electrode strip includes:
a first layer of foam configured to contact the skin on the human subject and including multiple cutouts and hydrogels, wherein the cutouts are spacedly disposed in the first layer of foam, and the hydrogels are disposed in the cutouts; and
a second layer of foam,
wherein the flexible printed circuit board is disposed between the first layer of foam and the second layer of foam and the integrated electrodes are positioned corresponding to the cutouts of the first layer of foam and are in contact with the hydrogels in the cutouts.

17. The method of claim 13, wherein the peripheral electrode wires each include a first section and a second section, the first section being external to the electrode strip and the second section being integrated into the electrode strip such that the connector includes a convergence of one or more second sections of the one or more peripheral electrode wires.

18. The method of claim 13, wherein the data recorder has a length of less than 6 centimeters, and a width of less than 6 centimeters.

19. The method of claim 13, wherein the data recorder includes a display, the method further comprising providing a status of one or both of the electrocardiogram or the data recorder with the display.

20. The method of claim 13, further comprising transmitting electrocardiogram data to one or more computing platforms with the data recorder.

21. The method of claim 20, wherein the data recorder is configured to wirelessly transmit the electrocardiogram data to the one or more computing platforms.

22. The method of claim 13, wherein the peripheral electrode wires are adjustable and long enough to allow each of the three individual peripheral electrodes to be pulled to the respective appropriate position for the electrocardiogram, thus meeting applicable standard 12-lead ECG measurement requirements.

23. The method of claim 13, wherein the peripheral electrode wires are disposed at the electrode strip before being pulled to the respective appropriate position for the electrocardiogram.

* * * * *